United States Patent
Leivseth et al.

[11] Patent Number: 6,059,740
[45] Date of Patent: May 9, 2000

[54] METHOD FOR DIAGNOSING AND TESTING/TRAINING PELVIC FLOOR MUSCULATURE

[76] Inventors: Gunnar Leivseth, Frognersatervn. 54A, N-0387 Oslo; Ole Olsen, Fiolveien 27, N-3970 Langesund, both of Norway

[21] Appl. No.: 09/078,106

[22] Filed: May 13, 1998

[30] Foreign Application Priority Data

May 11, 1998 [NO] Norway .................................. 982134

[51] Int. Cl.⁷ .................................................. A61B 5/103
[52] U.S. Cl. .......................................... 600/591; 600/587
[58] Field of Search ...................................... 600/591, 587

[56] References Cited

U.S. PATENT DOCUMENTS

| | | | |
|---|---|---|---|
| 3,933,147 | 1/1976 | Du Vall et al. | 600/591 |
| 4,050,449 | 9/1977 | Castellana et al. | 600/591 |
| 4,362,167 | 12/1982 | Nicolai et al. | 600/591 |
| 4,566,465 | 1/1986 | Arhan et al. | 600/591 |
| 4,682,609 | 7/1987 | Parsons | 600/591 |
| 4,873,990 | 10/1989 | Holmes et al. | 600/591 |
| 4,909,263 | 3/1990 | Norris | 600/591 |
| 5,154,177 | 10/1992 | Eisman et al. | 600/591 |
| 5,433,216 | 7/1995 | Sugrue et al. | 600/591 |
| 5,674,238 | 10/1997 | Sample et al. | 600/591 |
| 5,733,230 | 3/1998 | Sawchuck et al. | 600/591 |
| 5,787,892 | 8/1998 | Dabney | 600/591 |
| 5,846,211 | 12/1998 | Sakaguchi et al. | 600/587 |

*Primary Examiner*—Paul J. Hirsch
*Attorney, Agent, or Firm*—Ladas & Parry

[57] ABSTRACT

A measurement and training apparatus to be inserted in the vagina or rectum for diagnostic and pelvic musculature training purposes, comprises, two axially split halves of a substantially cylindrical body, kept at an adjustable distance from each other. A strain gauge measures a force perpendicular to the axis of the apparatus. The measurement is executed in a flexural mode where a forward end of one of the halves is bent toward the other half with a small deflection.

3 Claims, 3 Drawing Sheets

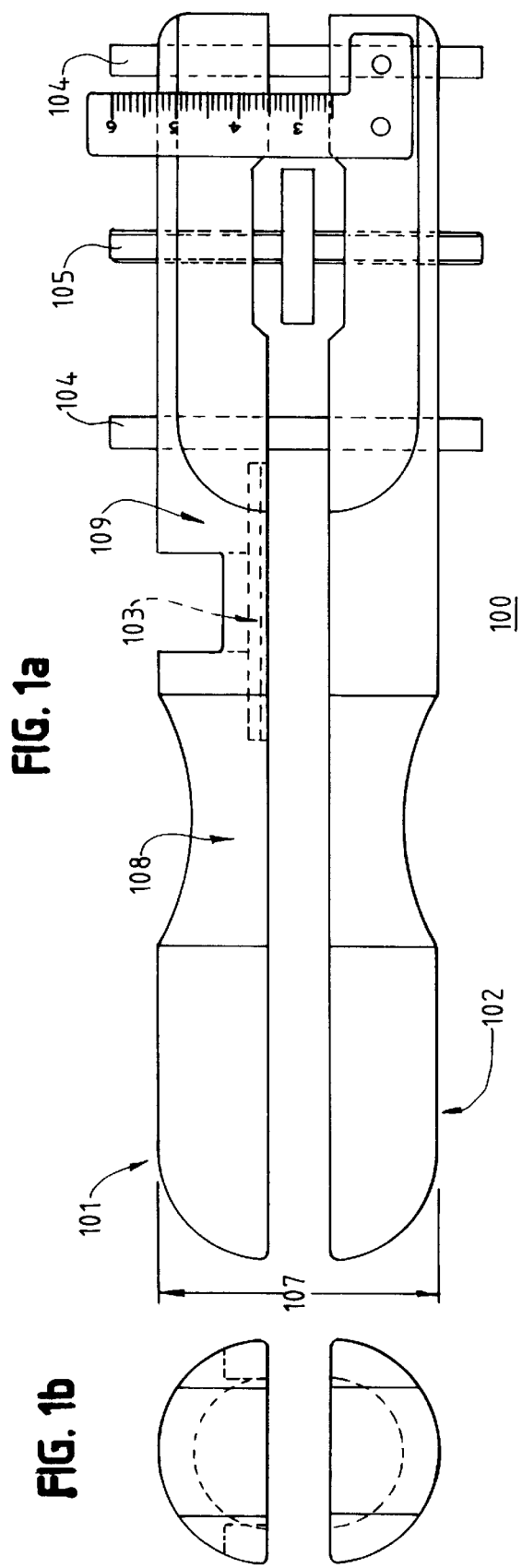

METHOD FOR DIAGNOSING AND TESTING/TRAINING PELVIC FLOOR MUSCULATURE

BACKGROUND OF THE INVENTION

This patent application is related to an apparatus and a set of parts used for diagnosing and testing/training pelvic floor musculature (tissue). It also includes a method for monitoring training of the pelvic floor in the absence of specialists.

During the last 50–60 years, it has been known that weakness in the pelvic floor tissue is one of the cause of urine leakage. During this time there has been an attempt to develop various measuring devices to help find the causes of the leakage, and to develop improved methods for evaluating the force in the pelvic floor in a reproducible and quantitative manner. These improvements would help specialists determine which persons should be treated in a conservative manner, and which persons should be treated operatively. Without knowledge of the normal and abnormal mechanical conditions in the pelvic floor, as well as the normal physiological and patohysiological conditions, this is problematic.

The most common method for evaluating the function of the pelvic floor is manual palpation. Such a method provides no reliable parameters, and the variation between different investigators is large.

Balloons have been used, and are still in use. Balloons are inserted into the vagina or the rectum. Since the balloon senses pressure changes without regard to directions, these results are also associated with large uncertainty. Additionally, one cannot know the changes of the balloon diameter during a test, nor the physical characteristics or the balloon. This has the consequence that it is not possible to calculate pelvic floor force from the pressure measurements.

Tubes working as electromyographic measurement electrodes have also been used. This method is also associated with a large uncertainty, since the electrical activity in the pelvic floor musculature is not proportional to the force output. In addition, great measurement uncertainty arises when the vaginal tissue moves relative to the inserted EMG sensor, i.e., a movement-induced increase in EMG activity arises, which increase is not related electrical activity in the tissue.

Conical devices that are inserted in the vagina have also been used. These conical devices have various weights. The weight is in the rage of 20 to 100 grams. Using these conical devices, one obtains a measure of the indirect force in the pelvic floor musculature. That is, if a conical device weighing e.g. 100 grams cannot be held in its place in the vagina, and falls out, the force output is less than 100 grams.

Important physiological and mechanical parameters of the pelvic floor musculature are not measured when the above methods are used. This is important since several conditions in the pelvic floor musculature may cause urine leakage. Therefore, it is important to obtain several measures of the pelvic floor function, both passive and active characteristics, like passive and active length/force-ratios.

Training of the pelvic floor musculature, usually prescribed by physicians, also has certain limitations; the persons may have trouble controlling whether they use the pelvic floor musculature, nor do they have any information regarding how large a force this musculature develops. Several different methods have been developed, all of them having the following weaknesses in general:

i) uncertainty whether the pelvic floor musculature is actually trained ii) uncertainty regarding the training load iii) uncertainty regarding intensity and duration of each training session.

SUMMARY OF THE INVENTION

We have developed a new measuring apparatus intended to measure the active and passive mechanical and physiological characteristics of the pelvic floor. The purpose of the new measuring equipment is that it is possible to use the measured parameters to improve diagnostics regarding urine leakage, and to optimize training so as to give the patients an optimum treatment as early as possible. In addition, variants of this measurement apparatus may be used for personal training of the pelvic floor musculature. That is, the persons are not dependent on skilled personnel to be able to carry out an adequate training session.

BRIEF DESCRIPTION OF THE DRAWINGS

FIG. 1a shows the structure of a preferred embodiment of the measurement and training apparatus of the invention;

FIG. 1b is a cross-sectional view of the preferred embodiment of FIG. 1a;

DETAILED DESCRIPTION OF THE INVENTION

Figure 1C:
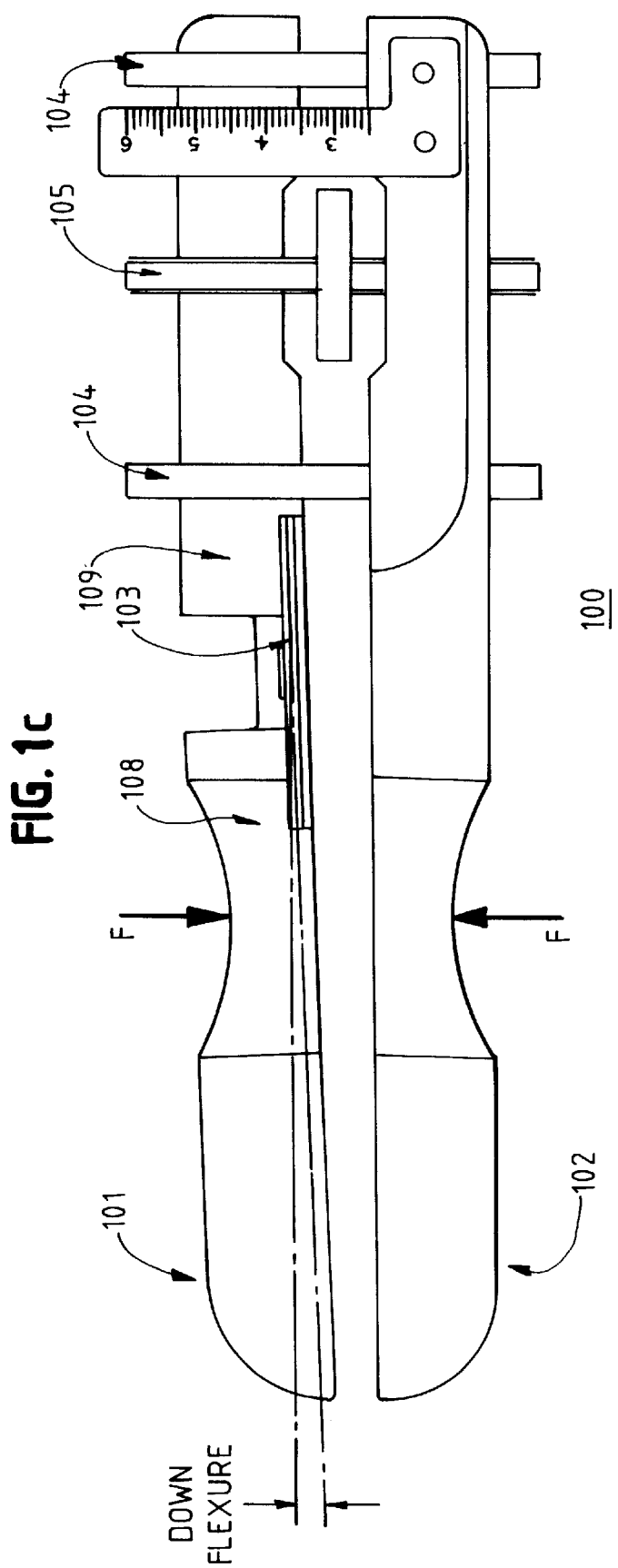
FIG. 1c shows the same embodiment as FIG. 1a, however in a situation with a flexural load.

FIG. 1a shows the structure of the measurement apparatus.

In principle the sensor 100 is inserted into the vagina or the rectum.

The sensor consists of two semi-round, stiff rods 101, 102 that can be shifted mutually in parallel so that the diameter/opening 107 can be changed. The material of the measurement rods 101, 102 is such that it cannot be deformed. One of the measurement rods 101 is split in two parts 108, 109. This rod is thereafter spliced together using a material 103 with other physical characteristics than the measurement rods 101, 102. The material 103 that has been spliced into that one measurement rod 101, will flex during testing, so that the various forces can be measured passively and actively for various openings.

The rear part of the sensor contains three pins 104, 105 which have the effect that deformation of this part cannot occur. Both measurement rods 101, 102 can move freely relative to the two bracing pins 104. The center pin 105, which also takes part in bracing or stiffening the sensor, is used to regulate the diameter or opening 107 of the measurement sensor.

The sensor is connected to a signal processing system (not shown).

Figure 2A:
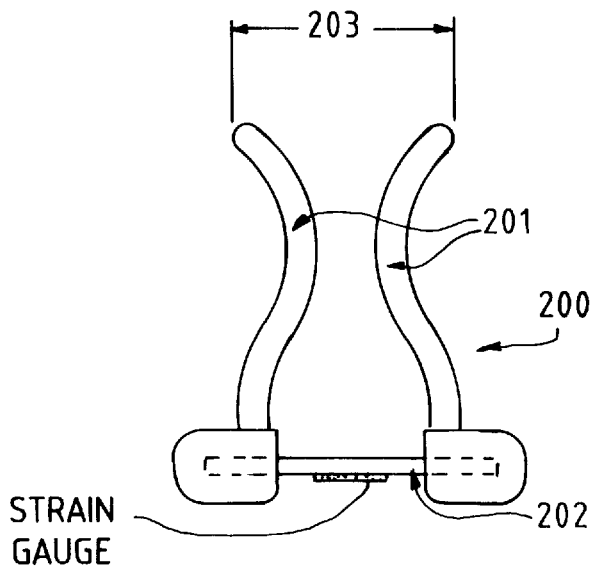
FIG. 2a shows an alternative embodiment of the measurement and training apparatus of the invention.
Figure 2B:
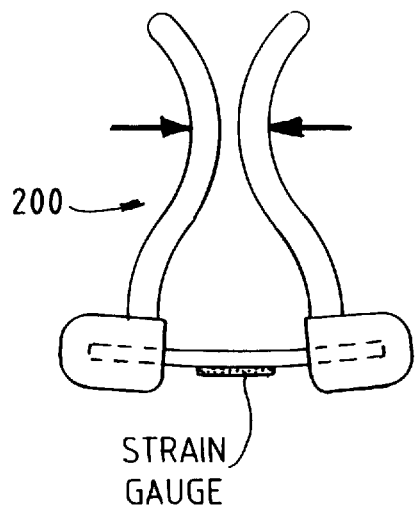
FIG. 2b shows the alternative embodiment of FIG. 2a with a flexural load.
Figure 2C:
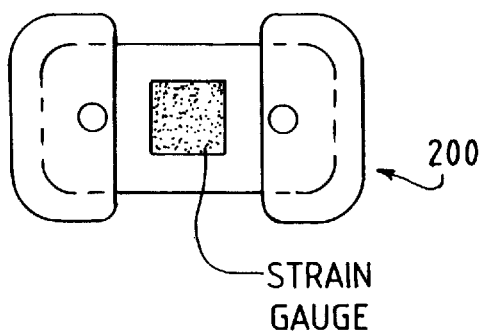
FIG. 2c shows a front view of the strain guage.

FIG. 2 discloses an alternative embodiment of a training apparatus 200 constructed using the same principles as the measurement apparatus. This training apparatus is also inserted into the vagina or rectum. By making connections to various measuring pins, where the horizontal part may have different lengths, one will, from the investigations, adjust the apparatus with an opening that is optimal for the individual person. The training apparatus is connected to a signal processing unit, so that the training person will receive information regarding correct execution of the exercises, and regarding the obtained force to be used in training, as well as the duration of each training session and when to end each training session. This entails that qualified personnel will not necessarily have to be present for stimulating/training the tissue. In continued training, it is possible to adapt the opening, dependent on achieved and measured changes in the active and passive characteristics of the pelvic floor, so that optimum training can be maintained all the time.

The rods 201 are made of a material that is substantially rigid. The rods are threaded onto the metal calibrating plate 202. The opening 203 in the apparatus used for personal training is adapted individually by preparing the metal calibrating plate 202 in various lengths. By threading these rods 201 onto the metal calibrating plate 202, with different lengths for the metal calibrating plate 202, we will obtain an individual opening of the training apparatus so as to provide optimal training/treatment of the active and passive characteristics of the pelvic floor.

The metal calibrating plate 202 has certain physical characteristics used for threading the rods on to it as described earlier. The metal plate will yield insignificantly, so that dynamic training of the musculature can occur.

What is claimed is:

1. An apparatus to be inserted in the vagina or rectum to measure passive and active characteristics of the pelvic floor comprising:

a first semi-round rod;

a second semi-round rod; and a means for coupling the first semi-round rod in parallel to the second semi-round rod, wherein said apparatus has a substantially round profile, the first semi-round rod and the second semi-round rod define an opening with a variable diameter, and further wherein a force corresponding to the passive and active characteristics of the pelvic floor is measured perpendicular to a longitudinal axis of the apparatus by determining a change in the variable diameter.

2. The apparatus of claim 1, wherein the variable diameter is adjustable so as to provide individual adaptation.

3. The apparatus of claim 2 wherein the means for coupling the first semi-round rod in parallel to the second semi-round rod is a calibrating plate, and the variable diameter of the apparatus can be adapted by utilizing different size calibrating plates thereon.

* * * * *